United States Patent
Hemmings

(10) Patent No.: US 10,145,763 B2
(45) Date of Patent: Dec. 4, 2018

(54) TOOL AND METHOD FOR ALIGNING A TISSUE PLANE FOR MICROTOMY

(71) Applicant: Kurt Hemmings, Montreal (CA)

(72) Inventor: Kurt Hemmings, Montreal (CA)

( * ) Notice: Subject to any disclaimer, the term of this patent is extended or adjusted under 35 U.S.C. 154(b) by 130 days.

(21) Appl. No.: 15/036,999

(22) PCT Filed: Dec. 23, 2014

(86) PCT No.: PCT/CA2014/051255
§ 371 (c)(1),
(2) Date: May 16, 2016

(87) PCT Pub. No.: WO2015/100493
PCT Pub. Date: Jul. 9, 2015

(65) Prior Publication Data
US 2016/0299039 A1     Oct. 13, 2016

Related U.S. Application Data

(60) Provisional application No. 61/921,816, filed on Dec. 30, 2013.

(51) Int. Cl.
*G01N 1/00*       (2006.01)
*G01N 1/06*       (2006.01)
(Continued)

(52) U.S. Cl.
CPC .......... *G01N 1/06* (2013.01); *A61B 10/0233* (2013.01); *G01N 1/286* (2013.01); *G01N 1/36* (2013.01);
(Continued)

(58) Field of Classification Search
CPC ...................................................... G01N 1/00
See application file for complete search history.

(56) References Cited

U.S. PATENT DOCUMENTS 3,733,948 A     5/1973   Pickett
4,695,339 A     9/1987   Rada
(Continued)

FOREIGN PATENT DOCUMENTS

EP     0937975 A2     8/1999
PL     222279 B1      4/2012

OTHER PUBLICATIONS

English language translation of PL 222279.
The Hague; Supplementary European Search Report; dated Jun. 29, 2017.

*Primary Examiner* — Jyoti Nagpaul
(74) *Attorney, Agent, or Firm* — Price Heneveld LLP

(57) ABSTRACT

A tool and a method are provided, for applying a correction on a resection margin of a tissue block, in order to align the resection margin with the cutting plane of a microtome. The correction is determined using an embedding block having been cut by the microtome. The tool comprises a base, a chuck receiver, a positioning assembly comprising a flat surface and a bi-axial pivoting assembly operatively connected to one of the chuck receiver and the positioning assembly. The positioning assembly and the chuck receiver are movable one relative to the other for pressing the embedding block between said flat surface of the positioning assembly and the top surface of the chuck, for tilting the bi-axial pivoting assembly according to a compensating angle indicative of the correction to make.

18 Claims, 10 Drawing Sheets

(51) Int. Cl.
*A61B 10/02* (2006.01)
*G01N 1/28* (2006.01)
*G01N 1/36* (2006.01)

(52) U.S. Cl.
CPC .............. *G01N 2001/065* (2013.01); *G01N 2001/2873* (2013.01)

(56) References Cited

U.S. PATENT DOCUMENTS

| | | |
|---|---|---|
| 5,776,298 A | 7/1998 | Franks |
| 6,568,307 B1 | 5/2003 | Guenther et al. |
| 7,059,139 B1 | 6/2006 | Marsing |
| 8,001,876 B1 | 8/2011 | Tabb et al. |
| 8,869,666 B2 * | 10/2014 | Yang .................. G01N 1/06 83/360 |
| 2002/0162337 A1 | 11/2002 | Peters |
| 2004/0152204 A1 | 8/2004 | Gauthier |
| 2008/0022831 A1 | 1/2008 | Watanabe et al. |
| 2012/0240737 A1 | 9/2012 | Yang et al. |

* cited by examiner

TOOL AND METHOD FOR ALIGNING A TISSUE PLANE FOR MICROTOMY

FIELD OF THE INVENTION

The present invention relates to the field of microtomy, and more particularly, the present invention relates to a tool and a method for aligning a tissue plane for Mohs micrographic surgery.

BACKGROUND OF THE INVENTION

Mohs micrographic surgery is a surgical technique for removing tumorous cells involving a repeated series of surgical excisions followed by microscopic examination of the tissue to assess if any tumorous cells remain. Essentially, the examination of the tissue during the procedure informs the surgeon where to remove tissue next and the surgeon performing the procedure is generally also the pathologist reading the tissue specimen slides.

Mohs surgical procedure typically involves the following steps, represented by FIGS. 1A to 1G. In step 1A, narrow resection margins are made around a grossly identifiable tumor. In step 1B, notches are made in the tissue sample and in surrounding normal tissue for conserving orientation during the procedure. In step 1C, the resected tumor is prepared in such a way that the complete resection margin is presented in one plane. At this point, colored inks are used to identify the notches. In step 1D, a microscope slide is made from the prepared sample that shows the path of the surgeon's knife. In step 1E, the slide is interpreted under a microscope for the presence of tumorous cells. In step 1F, the areas having tumorous cells are mapped on a graphic representation of the surgical site. In step 1G, the surgeon follows the map and removes remaining tumorous areas, where needed. The steps are repeated until no tumorous cells remain.

The goal of Mohs surgery is to completely remove all tumor tissues with the minimal amount of tissue loss. By examining complete on face tissue margins, the surgeon can be confident that the tumor is completely excised. By removing the tissue in multiple, very thin layers, the point at which no tumor remains will become obvious with the least amount of tissue excised.

The Mohs surgeon, also acting as pathologist, relies on the microscope slide prepared by a technician for diagnosis. However, the task of preparing an accurate representation of the resection margin has multiple pitfalls. More particularly, errors of flatness and errors of knife alignment are not resolved by known techniques presented hereinbelow.

In the Cryoembedder technique, also described in U.S. Pat. No. 7,059,139 issued to Marsing et al., a cryoembedder consists of a two-part jig that can accept the cryostat chuck on one part and a smooth disk on the second part. The tissue is frozen with the resection margin down on the smooth disk and the disk is placed on one of the jig faces. The cryostat chuck is placed in the other jig face and covered with embedding medium. When the embedding medium begins to freeze, the two jig faces are brought together and the sample to the chuck is frozen. Once frozen, the jig is separated and the smooth disk is broken free from the chuck-specimen-disk sandwich. The chuck is then ready for sectioning. Unfortunately, the Cryoembedder technique assumes that the object head is parallel to the knife holder, and due to the sliding fit clearance of the alignment pins of the jig, the faces may not always be parallel.

Also known as the Slide technique, the tissue is frozen flat against a glass microscope slide with the resection margin down against the slide. The technician is able to look under the slide to see if the surface of the tissue is making proper contact with the slide and corrections can be made before proceeding with the study. The slide is placed on the freeze bar for freezing. An embedding medium is poured around and over the tissue. A chuck is placed in the freezing bar and covered in embedding medium. As soon as the embedding medium begins to solidify on the slide, the tissue-slide block is flipped over to freeze on top of the chuck. Alternatively, the tissue covered in embedding medium is allowed to freeze completely. The slide is then removed from the cryostat and a warm hand is used under the glass slide to soften the tissue-embedding medium block. The tissue-embedding medium block is then freed from the glass. The tissue-embedding medium block is placed back in the cryostat and the chuck is placed in the freeze bar. The embedding medium is added on top of the chuck and as it freezes, the tissue-embedding medium block is placed on the chuck resection margin side up. However, one drawback with the Slide technique is that the tissue is frozen flat but not aligned with the knife.

In the Miami Special technique, a plier style (scissor, clamp) tool with wide jaws is used. One of the jaws has a hole or slot for accepting a chuck. Tissue is frozen flat using any technique the technician prefers, such as in the Slide technique described above. The tissue-embedding medium block is freed from the slide and placed against the smooth jaw. A chuck with embedding medium is placed on the modified jaw and the two jaws are brought together by squeezing the handles together. The jaws are then submerged in liquid nitrogen to freeze the tissue-embedding medium block solid. The jaws are removed from the liquid nitrogen, opened and the chuck is removed for use. However, drawbacks of the Miami Special technique relate to the need for liquid nitrogen and the angle that the jaw closes at sets the plane of the resection margin in relation to the chuck. Thicker specimens are set at a greater angle than thinner specimens.

Many cryostat manufacturers include a heat extractor with their units in which a mobile heat sink device is used for flattening and speeding the freezing of specimens. In the Heat Extractor technique, the heat extractor is essentially a chrome-plated metal weight with a smooth flat underside that is kept in the cryostat in order to keep it cooled. In previous practices, a chuck with embedding medium was placed on the freeze bar. The tissue was placed on top of the solidifying embedding medium and then the heat extractor was place on top of the tissue to flatten and freeze it. In recent years, Mohs technicians have begun using the flat underside in the same manner as done in the Slide technique. However, the tissue quickly freezes to the cold metal surface. Once frozen, the tissue is covered with embedding medium and a chuck is prepared on the freeze bar with embedding medium. The two are brought together and the block quickly freezes. One drawback of the Heat Extractor technique is that it is hard to get the tissue to freeze at the correct angle to match the angle of the knife.

In the Precision Cryoembedding System technique, also described in US 2002/0162337 A1 originally assigned to Stephen Peters, there is a metal bar that has a series of shallow flat bottomed wells. The wells are cut with a tapered mill. All the surfaces are smoothly polished and, in conjunction with the sloped sides, the embedding medium is aided in breaking free. The tissue is frozen flat to the bottom of the well and is covered in embedding medium until the well is full. A chuck is placed upside down on top of the well, in order for the peripheral edge of the chuck to rest on the edges of the well, which keeps the face of the chuck parallel to the bottom of the well. Once frozen, the stem of the chuck is jarred and the tissue-embedding medium-chuck block is freed from the mold. The drawbacks associated with the Precision Cryoembedding System technique are that not all chucks work with this system, as some chucks are stemless, and it is not possible to compensate for the knife angle as the tissue is parallel to the chuck face.

In the Plastic Molds technique, similar to that of the Precision Cryoembedding System but with thin plastic molds, the transparent molds freeze slower and allow the technician to look under the mold to see if the tissue is making proper contact in the center of the mold. A chuck can be frozen to the top of the mold or the tissue block can be popped out from the mold and mounted using any other technique known in the art. However, some drawbacks of the Plastic Molds technique are slow freezing; the molds are too small for larger specimens and difficult to compensate for knife angles.

Other techniques known in the art, such as the technique described in U.S. Pat. No. 5,776,298 issued to Franks, have drawback similar to the techniques described above.

Thus, known techniques for microtomy in the field of Mohs micrographic surgery lack the full set of attributes needed for minimizing tissue loss in sectioning when the tissue is aligned on a chuck, while minimizing errors of flatness and errors of knife alignment. There therefore exists a need in the art for a tissue aligning tool and method for preparing a tissue plane on a chuck for microtomy which alleviates at least some of the drawbacks of the prior art. The aligning tool and method may also be used for other surgical procedures, such as examination of a kidney tissue, or any other procedure requiring aligning a tissue plane with a reference plane, such as a cutting plane.

SUMMARY OF THE INVENTION

The object of the present invention is to provide a tool and a method which satisfies at least one of the above-mentioned needs and is thus an improvement over other related alignment systems and/or methods known in the prior art.

In accordance with the present invention, the above mentioned object is achieved, as will be easily understood, by a tool and a method such as the one briefly described herein and such as the one exemplified in the accompanying drawings.

According to an aspect of the invention, a tool for aligning a resection margin with the cutting plane of a microtome is provided. The tool comprises a base, a chuck receiver, a positioning assembly and a bi-axial pivoting assembly. The chuck receiver is typically mounted to the base and is for receiving a chuck. As well known in the art, a chuck has a top surface for supporting embedding blocks. The bi-axial pivoting assembly operatively is connected to the chuck receiver or to the positioning assembly. The positioning assembly and the chuck receiver are movable one relative to the other for pressing the embedding block between a flat surface of the positioning assembly and the top surface of the chuck, so as to tilt the bi-axial pivoting assembly according to a compensating angle indicative of the correction to make. A locking mechanism allows locking the bi-axial pivoting assembly in the complementing position.

According to a possible embodiment of the tool, the bi-axial pivoting assembly is mounted to the base and comprises the chuck receiver.

According to a possible embodiment of the tool, the positioning assembly is lowerable toward the bi-axial pivoting assembly, for pressing the embedding block between the flat surface of the positioning assembly and the top surface of the chuck.

According to a possible embodiment of the tool, the bi-axial pivoting assembly is a ball-joint assembly.

According to a possible embodiment of the tool, the tool further comprises a chuck locking mechanism mounted on the chuck receiver, configured to lock the chuck in the chuck receiver. For example, the chuck receiver can include a threaded aperture and a locking pin, such that the threaded aperture receives the locking pin to lock the chuck in the chuck receiver. Of course, other locking mechanism can be considered, such as a high friction assembly between the bi-axial assembly and the base.

According to a possible embodiment of the tool, the positioning assembly can include a plate. The plate comprises a top surface and a lower surface, which includes the flat surface. The plate preferably has a tapered end, for providing increased clearance when removing the chuck from the chuck receiver.

According to a possible embodiment of the tool, the positioning assembly includes a guiding assembly mounted onto to the base, configured to cause the positioning assembly to move perpendicularly to the base. The guiding assembly can include at least one shaft mounted perpendicular onto to the base, the plate being provided with corresponding aperture(s) for receiving each of the least one shaft. The shaft(s) allows the positioning assembly to slide thereon. Preferably, the tool includes two shafts. The shaft(s) and the plate are also preferably removably connected.

Preferably, the plate has its top surface opposite to the lower, flat surface. The plate can include at least one flange positioned coaxially with each aperture. The flange(s) extend outwardly from each surface, in order to maintain the flat surface perpendicular to the at least one shaft.

The tool can comprise the chuck. The chuck typically comprises a platform, and may include a stem extending therefrom. The platform has a sidewall which is preferably provided with a groove for positioning the chuck in a predetermined orientation in the chuck receiver or in the microtome.

According to another aspect of the present invention, a method is provided for aligning a resection margin of a tissue block with the cutting plane of a microtome in a cryostat. The method comprises the steps of:

a) providing an embedding block having opposed first face and second face, the second face resting on the top surface of a chuck;

b) placing the chuck in the microtome and cutting the first face of the embedding block, the cut first face of the embedding block forming thereafter an angle with the top surface of the chuck, said angle corresponding to a compensating angle between the top surface of the chuck and the cutting plane of the microtome;

c) determining an angle formed between the cut first face of the embedding block and the top surface of the chuck thereby corresponding to a misalignment angle; and d) placing the chuck in a tool comprising a positioning assembly, the positioning assembly comprising a flat surface, the tool positioning the top surface of the chuck at an angle corresponding to the misalignment angle relative to the flat surface of the positioning assembly.

According to a preferred embodiment of the method, the step of determining the angle in step c) comprises the sub-steps of:

placing the chuck with embedding block, cut in previous step, in a tool comprising bi-axial pivoting assembly;

lowering a horizontal flat surface toward the bi-axial pivoting assembly until the horizontal flat surface presses on the cut first face of the embedding block, thereby tilting the bi-axial pivoting assembly in a complementing position, an angle formed between the horizontal flat surface of the positioning assembly and the top surface of the chuck thereby corresponding to a misalignment angle; and locking the bi-axial pivoting assembly in the complementing position and removing the embedding block from the tool.

Preferably, cutting the first or exposed face of the embedding block is made by cutting its entire surface. The embedding block used in step a) may solely comprises embedding medium or it may include the tissue sample. In the latter case, the embedding block corresponds to the tissue block.

The method may further comprise the steps of:

placing a tissue sample having been previously frozen and flattened on the top surface of the chuck;

embedding the tissue sample with embedding medium to form the tissue block having opposed first face and second face, the first face of the tissue block corresponding to the resection margin of the tissue sample, the second face resting on the top surface of the chuck, placing the chuck with the tissue block in the tool comprising the positioning assembly;

moving the horizontal flat surface relative to the first face of the tissue block until the horizontal flat surface presses on the first face of the tissue block, thereby remodeling the tissue block such that the first face of the tissue block being parallel to the flat surface and forming a remodeling angle between the first face of the tissue block and the top surface of the chuck, said angle corresponding to the misalignment angle;

allowing the embedding medium of the tissue block to freeze; and removing the chuck from the tool and placing the chuck in the microtome for cutting layers of the tissue block, the first face of the tissue block, remodelled in previous step, being therefore parallel to the cutting plane of the microtome, the misalignment angle of the tissue block cancelling the compensating angle between the cutting plane and top surface of the chuck.

The objects, advantages and features of the present invention will become more apparent upon reading of the following non-restrictive description of preferred embodiments thereof, given for the purpose of exemplification only, with reference to the accompanying drawings.

DESCRIPTION OF PREFERRED EMBODIMENTS OF THE INVENTION

Figure 1A:
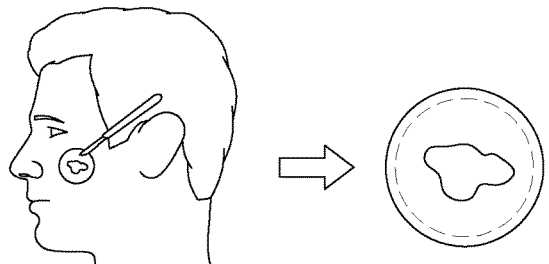
FIGS. 1A to 1G schematically illustrates the general steps of a Mohs surgical procedure (PRIOR ART).
Figure 1B:
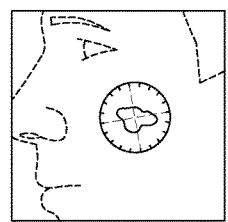
Figure 1C:
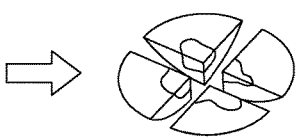
Figure 1D:
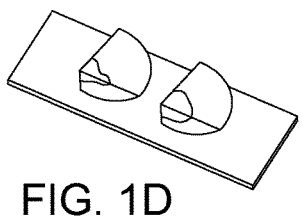
Figure 1E:
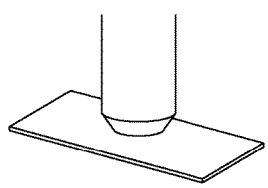
Figure 1F:
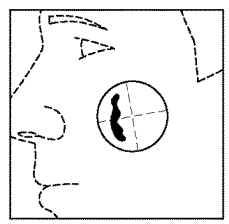
Figure 1G:
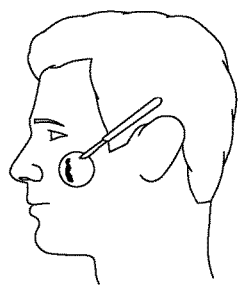

It is to be understood that certain descriptions of the present invention have been simplified to illustrate only those elements and limitations that are relevant to a clear understanding of the present invention, while eliminating, for purposes of clarity, other elements. Those of ordinary skill in the art, upon considering the present description of the invention, will recognize that other elements and/or limitations may be desirable in order to implement the present invention. However, because such other elements and/or limitations may be readily ascertained by one of ordinary skill upon considering the present description of the invention, and are not necessary for a complete understanding of the present invention, a discussion of such elements and limitations is not provided herein. As such, it is to be understood that the description set forth herein is merely exemplary to the present invention and is not intended to limit the scope of protection.

It is worth mentioning that throughout the following description, when the article "a" is used to introduce an element, it does not have the meaning of "only one" it rather means of "one or more".

As used herein, the expression "resection" is intended to refer to surgical removal of a portion of any part of the body. There can be a second resection done in the lab called a pathological resection margin and in that case the initial cut becomes the surgical resection margin.

As used herein, the expression "resection margin" is the margin of apparently non-tumerous tissue around the cancerous portion of a tissue sample that has been surgically removed.

As used herein, the term "tissue" is intended to refer to any group of biological cells that perform a similar function.

As used herein, the term "microtomy" is intended to refer to the science or practice of preparing extremely thin slices of tissue, etc., cut by a microtome, for study under the microscope.

As used herein, the term "microtome" is intended to refer to a tool used to cut extremely thin slices of material, known as sections. Microtomes are used in microscopy, allowing for the preparation of samples for observation under transmitted light or electron radiation. Microtomes use steel, glass, or diamond blades depending upon the specimen being sliced and the desired thickness of the sections being cut. Also, the specimen may be raised and lowered across a stationary blade. Alternatively, some models move a blade across a stationary sample and others use a vibrating blade to cut through harder samples.

Moreover, although the preferred embodiment of the present invention as illustrated in the accompanying drawings comprises components such as a bi-axial pivoting assembly, a plate, a base, etc., and although the preferred embodiment of the tool to align the resection margin with the cutting plane of a microtome and corresponding parts thereof consists of certain geometrical configurations as explained and illustrated herein, not all of these components and geometries are essential to the invention and thus should not be taken in their restrictive sense, i.e. should not be taken as to limit the scope of the present invention. It is to be understood, as also apparent to a person skilled in the art, that other suitable components and cooperations thereinbetween, as well as other suitable geometrical configurations may be used for the tool to align the resection margin with the cutting plane of a microtome according to the present invention, as will be briefly explained herein and as can be easily inferred herefrom, by a person skilled in the art, without departing from the scope of the invention.

In the following description, similar features in the drawings have been given similar reference numerals. The embodiments, geometrical configurations, materials mentioned and/or dimensions shown in the figures or described in the present description are preferred embodiments only, given for exemplification purposes only.

Furthermore, the order of the steps of the method described herein should not be taken as to limit the scope of the invention, as the sequence of the steps may vary in a number of ways, without affecting the scope or working of the invention, as can also be understood.

Devices known in the art are unable to keep the tissue plane of the sample parallel to path of the knife. They focus solely on keeping the tissue plane parallel to the face of the chuck, falsely assuming that the path of the blade is square with the chuck. The knife that cuts this face can be off by as much as 0.158° degrees (this was measured as 0.0185" displacement over a 6.6929" run), which results in a loss of 69μ (Microns) of tissue on a 25 mm wide tissue sample.

The coupling device on the object head of other devices known in the art pushes the chuck a much as 0.010" out of alignment over a 1.578" diameter chuck. This results in a 0.363° error and, to relate this to the previous example, equals 158μ of tissue loss for a 25 mm wide sample.

The ball detent that technicians rely on in the art to zero the object head can be off by as much 0.045" over a 1.950" face, and this equals 1.322° and a further 577μ of tissue loss for a 25 mm sample. The locking arm for the XY axial adjustments on the object head can push the object head face out another 30 to 50μ more.

Some of the tools known in the art use a sliding fit on their jigs to bring two faces together in a parallel plane but the tolerances of this 0.010" fit causes a 0.572° error or 250μ for a 25 mm sample.

If we were to compound these errors, a total of 854μ is obtained or at the very least with some errors cancelling others 300μ is obtained without considering the help or hindrance of the other tool.

A micron is a very small unit so these miss alignments might at first glance seem trivial. However, the tissue sections cut on the microtome are generally 5-7μ thick and an average cell is 10-15μ in diameter. It should be noted that a layer of 3 normal cells can make the difference between a false negative and a false positive for a broad group of diseases involving unregulated cell growth, such as cancer.

Broadly described, the tool for aligning the resection margin with the cutting plane of a microtome according to the present invention, as exemplified in the accompanying drawings, is a tool for applying a correction on a tissue block in order to align the resection margin of the tissue block with the cutting plane of a microtome. The correction is typically determined using an embedding block having been cut by the microtome, such that the actual cutting plane of the microtome is "transferred" to the cut embedding block.

For the sake of clarity, certain reference numerals have been omitted from the figures when they have already been identified in a preceding figure.

Figure 5A:
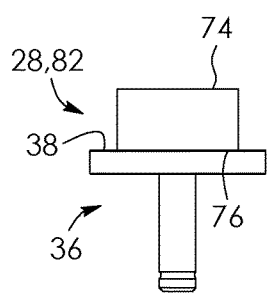
FIGS. 5A to 5J schematically illustrate the general steps of a method for aligning a resection margin with the cutting plane of a microtome, according to a possible embodiment.

Referring to FIG. 5A, a chuck 36 with an embedding block (28, 82) is shown. An embedding block typically consists of embedding medium which includes the tissue sample, with the resection margin of the tissue sample facing upwardly. In some cases, the embedding block may not include the tissue sample, and solely consists of frozen embedding medium, as will be explained in more detail below. Typically, when the embedding block comprises the tissue sample, it is referred to as a "tissue block".

The chuck 36 has a top surface 38 for supporting the block (28, 82). While the chuck shown in FIG. 5A is provided with a stem, other configurations of chucks are possible, as is well known in the art. The embedding block (28 or 32) has a first face 74 facing upwardly when placed on the chuck, and a second, opposite face 76 resting on the chuck. The first face 74 can also be referred to as the "exposed" or "resection" face of the block. When the embedding block includes a tissue sample, the first face 74 includes the resection margin of the tissue sample.

Figure 5B:
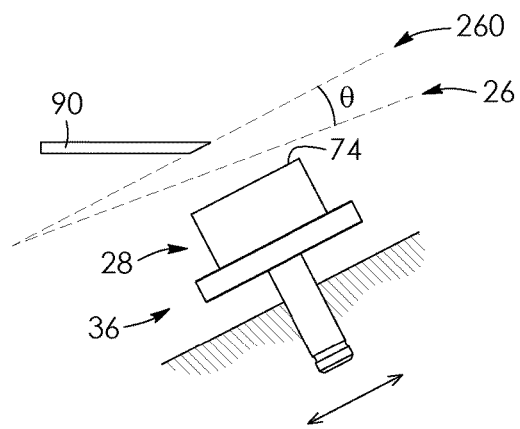

Referring to FIG. 5B, a schematic drawing of the blade 90 of a microtome and of the chuck 36 placed in the microtome is shown. As indicated by the arrow, the chuck can move back and forth relative to the blade 90 of the microtome, so as to slice thin layers of the tissue sample from the embedding block, similar to a meat slicer.

The cutting plane 26 is the actual cutting plane of the blade 90 in a microtome, and the theoretical cutting plane 260 is the ideal cutting plane which should be parallel to the first face 74 of the tissue sample, such that when the microtome slices layers of the tissue sample, the entire surface of the resection margin 24 of the tissue sample is cut.

As explained above, in theory, the cutting plane 26 of the microtome should be parallel to the top surface of the chuck 38, and the exposed face (or resection margin) of the tissue sample should also be parallel to the top surface of the chuck 38. The tissue sample is embedded in embedding medium, and, according to common practice, technicians will aim to freeze the embedding block 28 such that the top or exposed face of the block 74 is parallel to the top surface of the chuck 38.

However, in reality, the cutting plane 26 of microtome and the top surface of the chuck 38 are not parallel, and there is an angle between the two planes (i.e. cutting plane of microtome 26 and top surface of chuck 38 when placed in microtome). Thus, if the first surface 74 of the embedding block 28 is frozen such as to be as parallel as possible with the top surface of the chuck 38, there will be an error or misalignment angle θ between the cutting plane of the tool 26, and the exposed surface 74 of the embedding block 28.

The tool 20 and method of the present invention aims to align the first or resection face 24, 74 of the embedding block 28 with the actual cutting plane of the microtome blade. One possible way of achieving this alignment is by remodeling or reshaping the embedding block 28 such that the first/resection face 74 of the embedding block 28 is coplanar with the cutting plane of the microtome.

Method for Aligning the Resection Margin of a Tissue Block with the Cutting Plane of a Microtome in a Cryostat Referring now to FIGS. 5C to 5J, a method for aligning the resection margin of a tissue block 22 with the cutting plane 26 of a microtome in a cryostat will be described, according to a possible implementation.

The method may be divided into two main stages: 1) determining the misalignment angle, as illustrated in FIG.

Figure 6A:
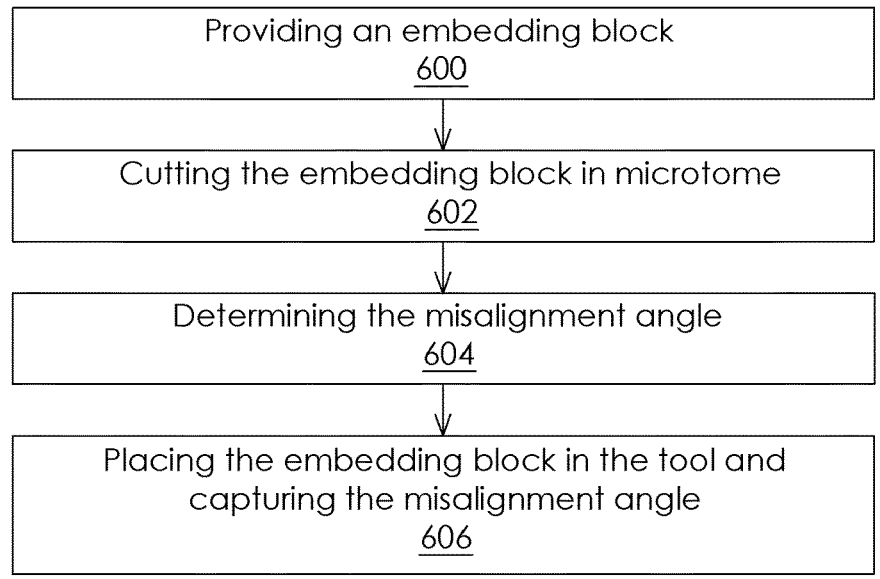
FIGS. 6A and 6B are block diagrams representing the different steps of the method, according to a possible embodiment.
Figure 6B:
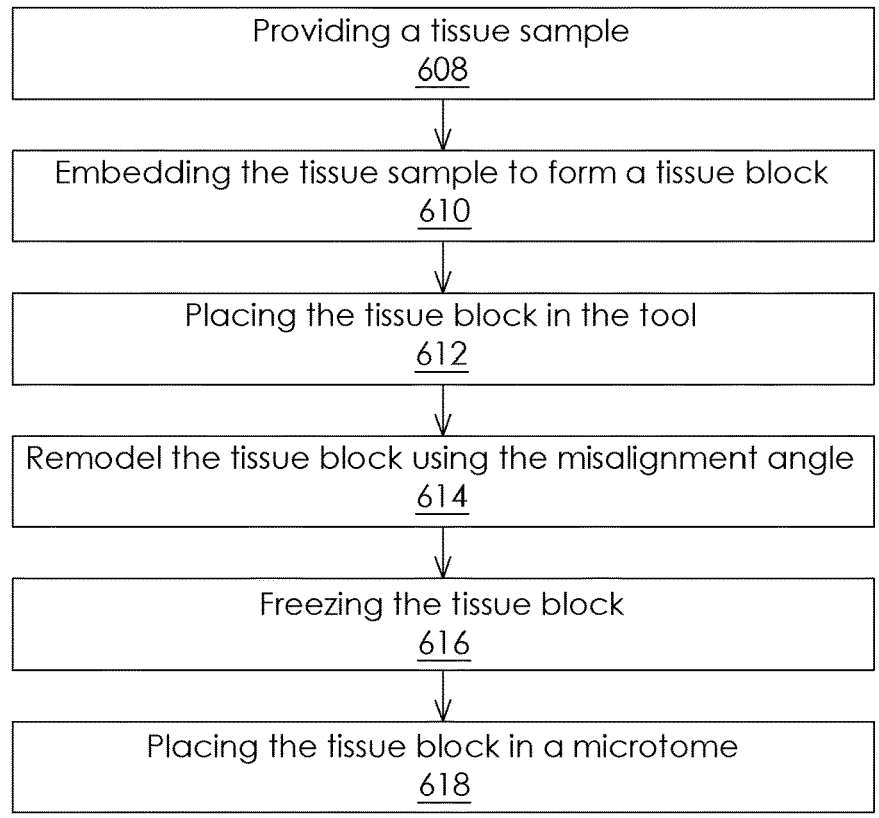

6A and 2) remodelling the tissue block 22 to compensate for the misalignment angle, as illustrated in FIG. 6B.

Figure 5C:
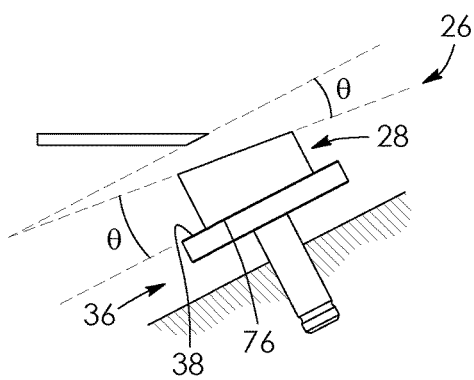

Referring to FIG. 5C, in a first stage of the method, an embedding block 28 is provided 600 and placed on the top surface of the chuck 38. In this step, the embedding block 28 does not necessarily comprise the tissue sample, since this step initially consists in determining the correction angle to apply for future tissue sample to be processed. The embedding block 28 has opposed first face 74 and second face 76. The second face 76 rests on the top surface of the chuck 38. The embedding block 28 can be made of any suitable material such as an embedding medium, a tissue block 22, polyvinyl alcohol and the like, as apparent to a person skilled in the art. The embedding block 28 may be used as a test block in order to capture the misalignment angle.

Still referring to FIG. 5C, the first face 74 of the embedding block 28 is preferably cut 602 across the entire surface of the first face 74 to reduce reading errors of the misalignment angle. The cut first face 74 of the embedding block 28 forms thereafter an angle with the top surface of the chuck 38, as illustrated in FIG. 5C, said angle corresponding to a compensating angle between the top surface 38 of the chuck 36 and the cutting plane 26 of the microtome.

The next step of the method is to determine 604 and reuse the misalignment angle. There are a number of ways to use to determine the misalignment angle. For example, by using a 3D image scanner or by using a tool comprising a bi-axial pivoting assembly 32 as the one described below and illustrated in FIG. 5D.

Figure 5D:
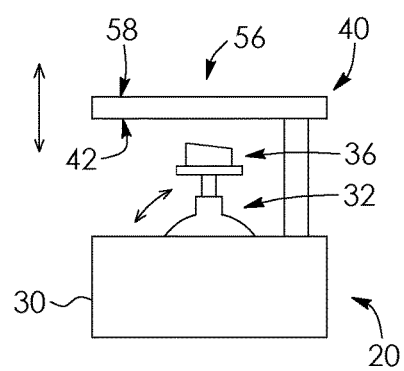

Referring to FIG. 5D, the chuck 36 is placed in the tool 20,606, comprising the bi-axial pivoting assembly 32. The bi-axial pivoting assembly 32 is mounted on to the base 30 and is free to rotate along the coplanar axis of the base 30. The tool 20 also comprises a positioning assembly 40 which includes a plate 56 having a horizontal flat surface 42 that can be moved vertically as shown in FIG. 5D.

Figure 5E:
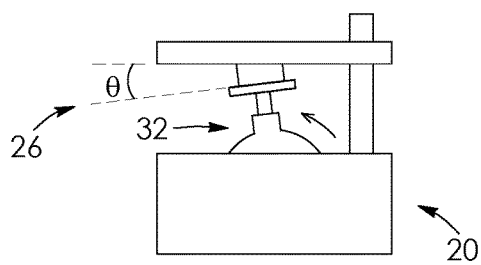
Figure 5F:
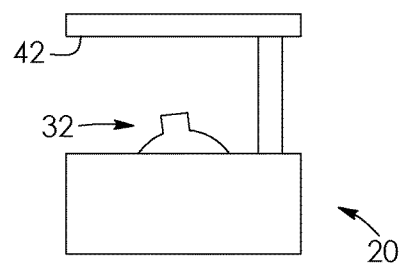

Referring to FIG. 5E, the plate is lowered until the horizontal flat surface 42 presses on the cut first face 74 of the embedding block 28, thereby tilting the bi-axial pivoting assembly 32 in a complementing position. At this point, the angle θ formed between the top surface 38 of the chuck 36 and the cut first face 74 corresponds to the misalignment angle defined in FIG. 5C. Once in this complementing position, the bi-axial pivoting assembly 32 can be locked and the chuck is removed, as illustrated in FIG. 5F.

Figure 5G:
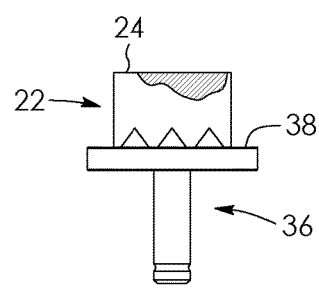

Referring to FIG. 5G, in a second stage of the method, a tissue block is provided 608 and placed on the top surface of the chuck 38. The tissue sample has a resection margin 24 corresponding to the lowermost portion of the sample cut by the surgeon. An embedding medium (23) is applied 610 on the tissue sample to form a tissue block 22. The tissue block 22 has an exposed/outer face, and a second, opposite face. The second face rests on the top of face of the chuck 36.

Figure 5H:
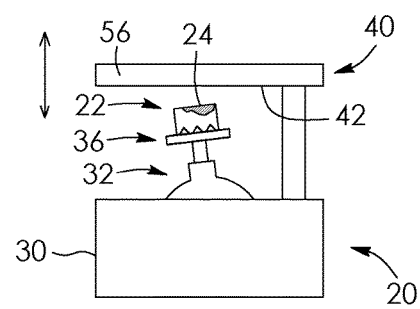
Figure 5I:
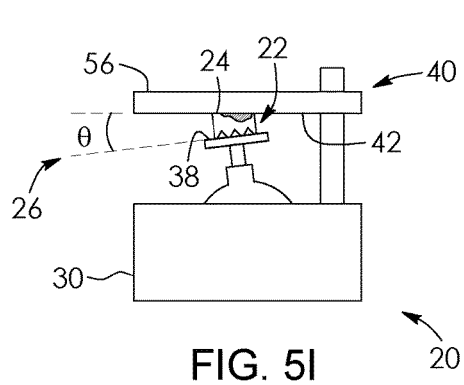

Referring to FIG. 5H, the chuck 36 is placed 612 in the tool 20 where the bi-axial pivoting assembly 32 was locked in the complementing position. At this stage, the plate of the positioning assembly is lowered until the horizontal flat surface 42 presses on the resection margin of the tissue block 22, thereby remodelling 614 the tissue block such that the resection margin 24 of the tissue block 22 is coplanar with the horizontal flat surface 42, as illustrated in FIG. 5I. The exposed face of the tissue block 22 can be remodelled or reshaped because the emdedding medium is not completely frozen at this stage, and can be thus be slightly remodelled by the flat surface of the positioning assembly, can in this case is comprised in the plate 56.

Referring to FIG. 5I, the remodelled tissue block 22 now has its expose face, corresponding to the resection margin 24 of the tissue sample, forming an angle θ with the top surface 38 of the chuck 36, where this angle corresponds to the misalignment angle. At this stage, the tissue block is allowed to freeze in the cryostat.

Figure 5J:
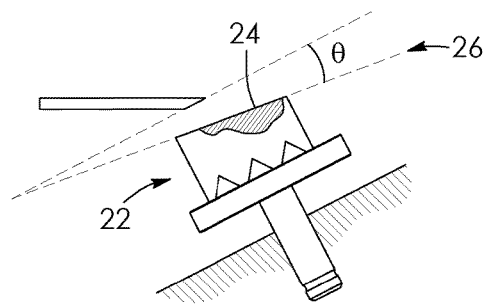

Referring to FIG. 5J, once the tissue block is frozen 616, the chuck 36 can be placed in the microtome to layer the tissue sample so as to start the examination of the tissue sample. At this point, the resection margin 24 of the block 22 is parallel with the actual cutting plane of the microtome blade eliminating or at least greatly reducing the error or the misalignment angle θ between the cutting plane of the tool 20, and the resection margin 24 of the tissue block 22.

Tool for Aligning the Resection Margin of a Tissue Lock with the Cutting Plane of a Microtome in a Cryostat Broadly described and referring to FIGS. 2A to 4B, there is shown the tool 20 for applying a correction on the resection margin 24 of a tissue block 22 in order to align the resection margin 24 with the cutting plane 26 of a microtome.

Figure 2A:
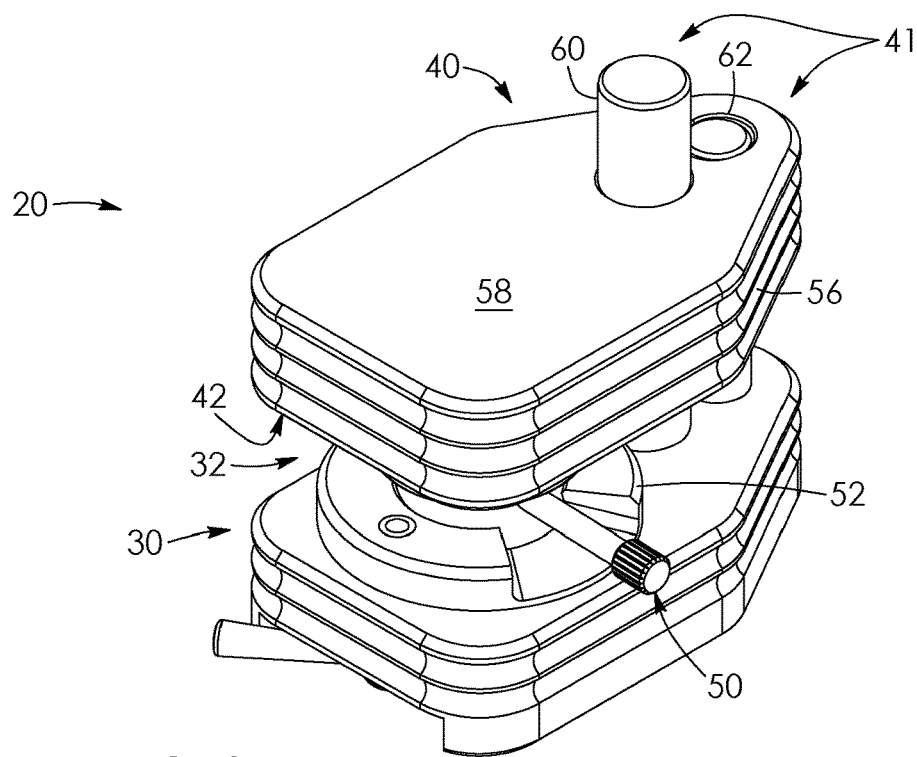
FIG. 2A is a perspective view of a tool, in accordance with a possible embodiment of the present invention.
Figures 4, 4A:
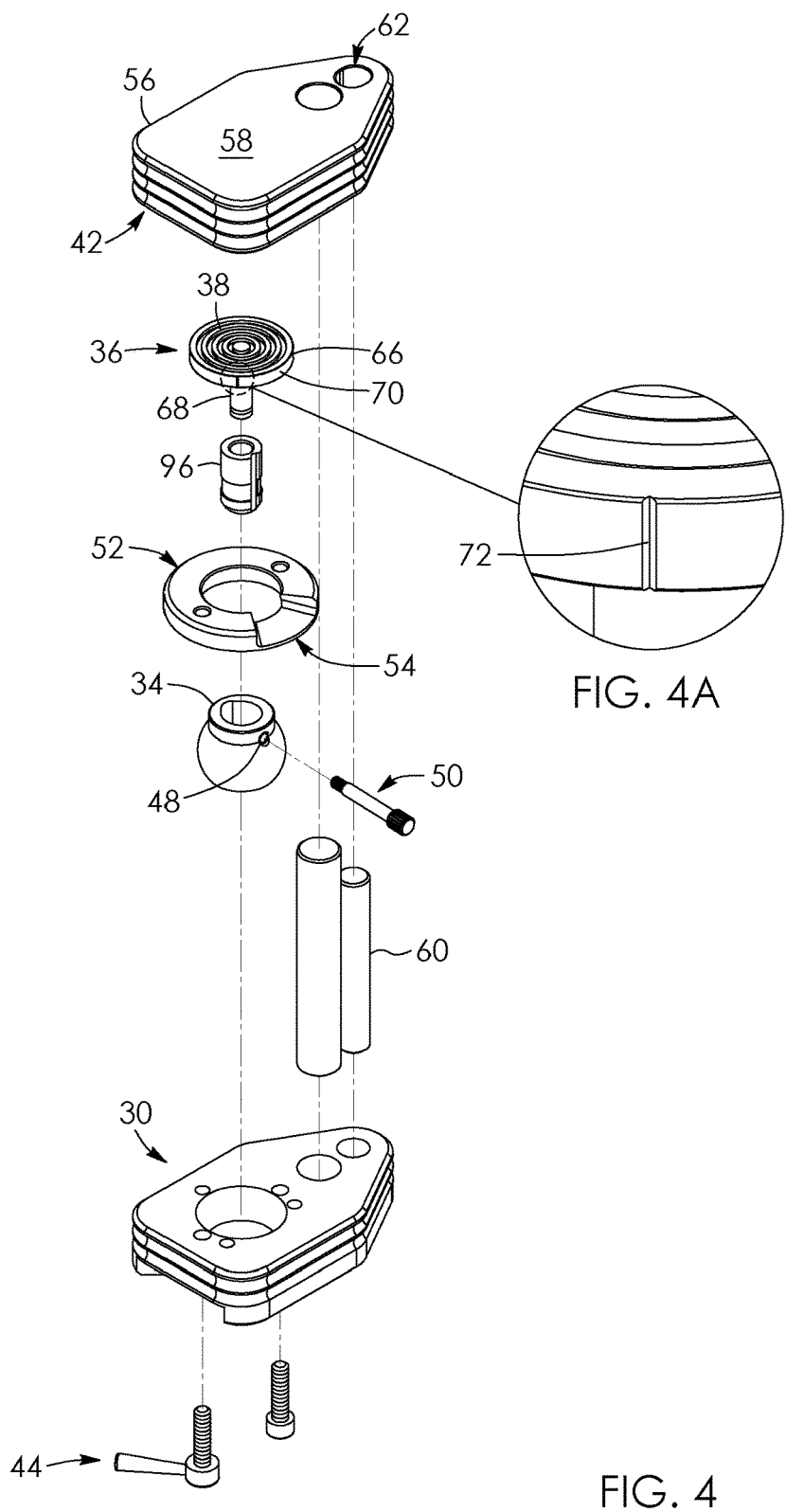
FIG. 4A is an exploded view of the tool shown in FIG. 2A.

Referring to FIGS. 2A and 4A, the illustrated tool 20 comprises a base 30, a positioning assembly 40 and a bi-axial pivoting assembly 32.

Figure 3A:
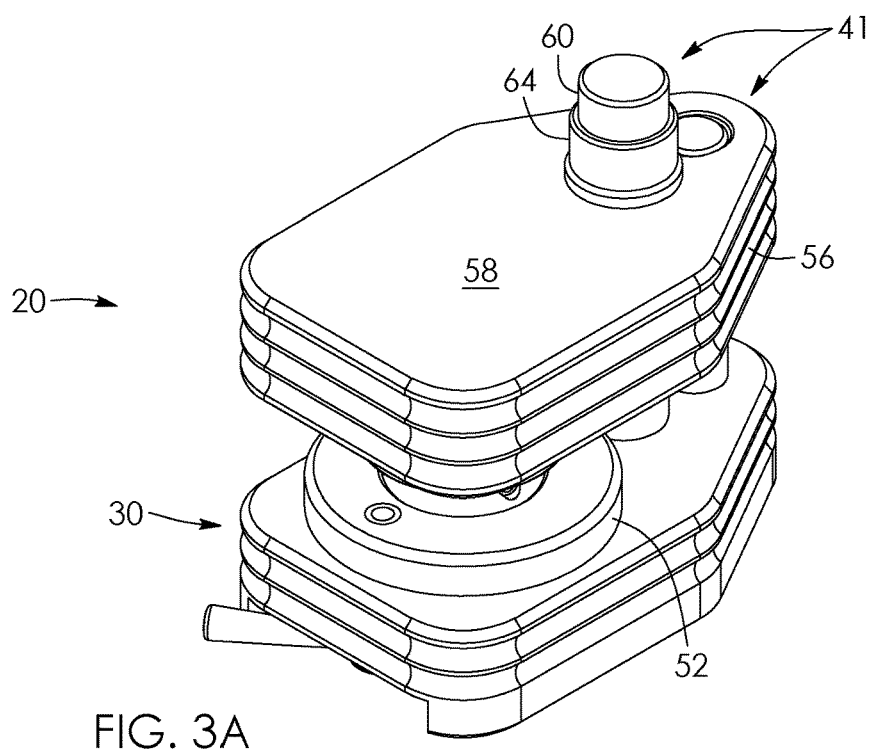
FIG. 3A is a perspective view of a tool in accordance with another embodiment of the present invention.
Figure 3B:
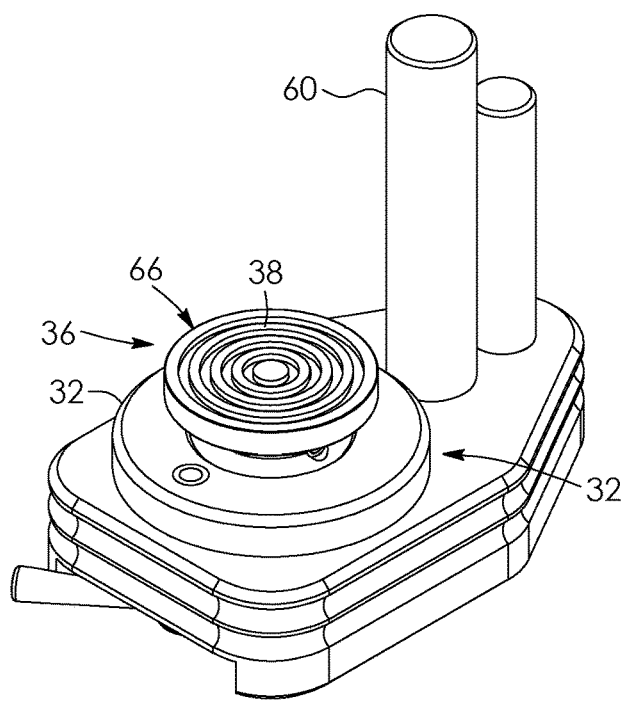
FIG. 3B is another perspective view of FIG. 3A, with an element removed.
Figure 3C:
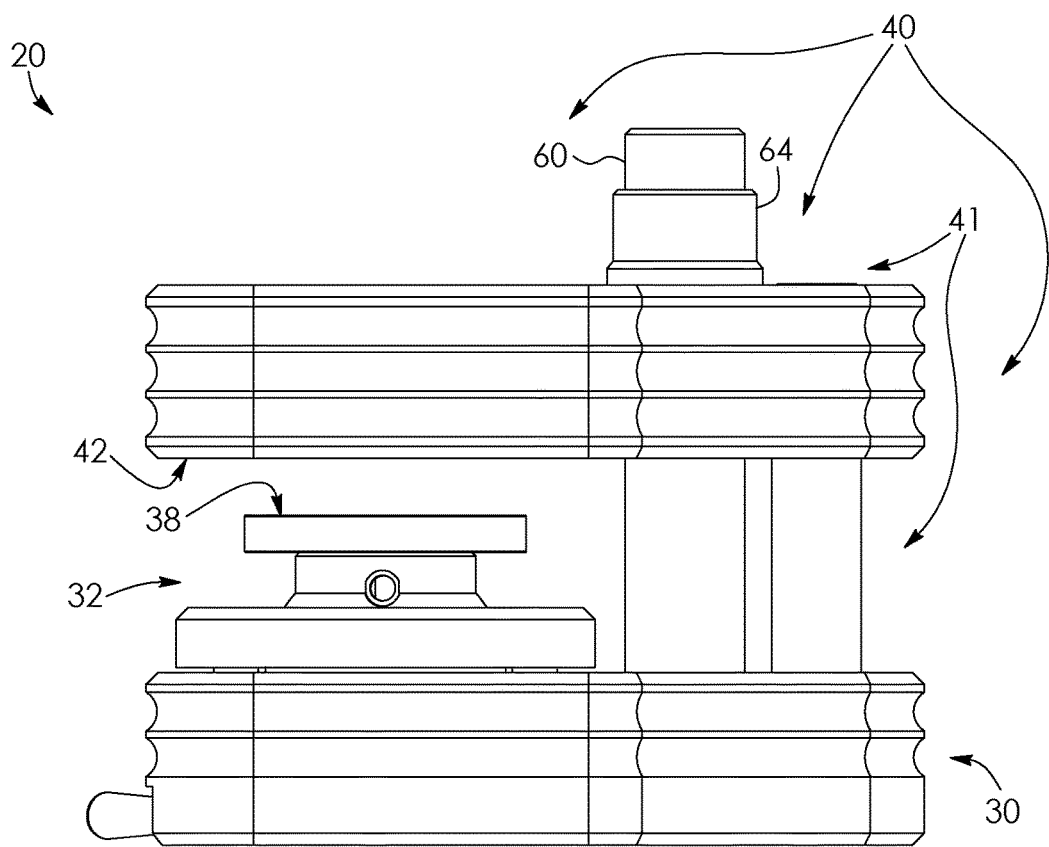
FIG. 3C is a side view of the tool of FIG. 3A.

The positioning assembly 40 includes a plate 56 that has a flat surface 42, and a guiding assembly 41. The flat surface 42 is used to press on a surface of a tissue block 22 or embedding block 28 to create a reference surface for angle measurements. The guiding assembly 41 is used to guide the relative movement between the flat surface 42 and the base 30. According to an embodiment, the guiding assembly may be mounted on the base 30 and comprises at least one shaft 60 and corresponding apertures 62 as illustrated in FIG. 4A. The guiding assembly may optionally comprise a rail system, a controlled robotic arm, or the like, as apparent to a person skilled in the art. The guiding assembly may also be mounted on a support other than the base 30 in order to control the orientation and position of the positioning assembly 40 and to move the positioning assembly 40 and/or the chuck receiver 34 relative to each other. Referring to FIG. 4A, the guiding mean comprises at least one shaft 60 mounted perpendicular onto to the base 30. The plate 56 comprises a corresponding aperture 62 for receiving each of the least one shaft 60. In this configuration, the guiding assembly allows the plate 56 to slide thereon to reach the tissue block 22 or the embedding block 28. In this configuration, the weight of the plate 56 allows the flat surface 42 to press on the tissue block 22 or the embedding block 28 in order to align the resection margin 24 or the first surface of the embedding block according to the compensating angle. Optionally, the plate 56 includes at least one flange 64 positioned coaxially with each aperture 62 and extending outwardly from each surface of the plate 56 in order to maintain the flat surface 42 perpendicular to the at least one shaft 60, as shown in FIG. 3A. The at least one shaft 60 and the plate 56 may also be removably connected. Optionally, the plate 56 may have a tapered end, as illustrated in FIG. 2A, to provide increased clearance when lifting the plate 56 and placing or removing the chuck 36. In this preferred embodiment, two shafts are mounted to the base 30.

The tool (20) also comprises a chuck receiver 34 that is operatively mounted to the base 30 for receiving a chuck 36. Referring to FIG. 4A, the chuck receiver comprises a threaded aperture and a locking pin 50 and is forming part of the bi-axial pivoting assembly. The chuck receiver may have different configurations such as a clamp, a press fitting mechanism and the like. The chuck receiver may also be mounted on the base 30 directly or being held by a device such as an arm and a clamp to receive the chuck 36. The chuck receiver may be mounted on the base 30 or on another support, as apparent to a person skilled in the art. In the configuration illustrated in FIG. 4A, a protrusion 52 is added to house the chuck receiver 34 in the bi-axial pivoting assembly. To facilitate the movement of the locking pin 50 around the bi-axial pivoting assembly 32, the protrusion 52 around the bi-axial pivoting assembly 32 may have a recess 54 to allow further movement of the locking pin 50.

Figure 4B:
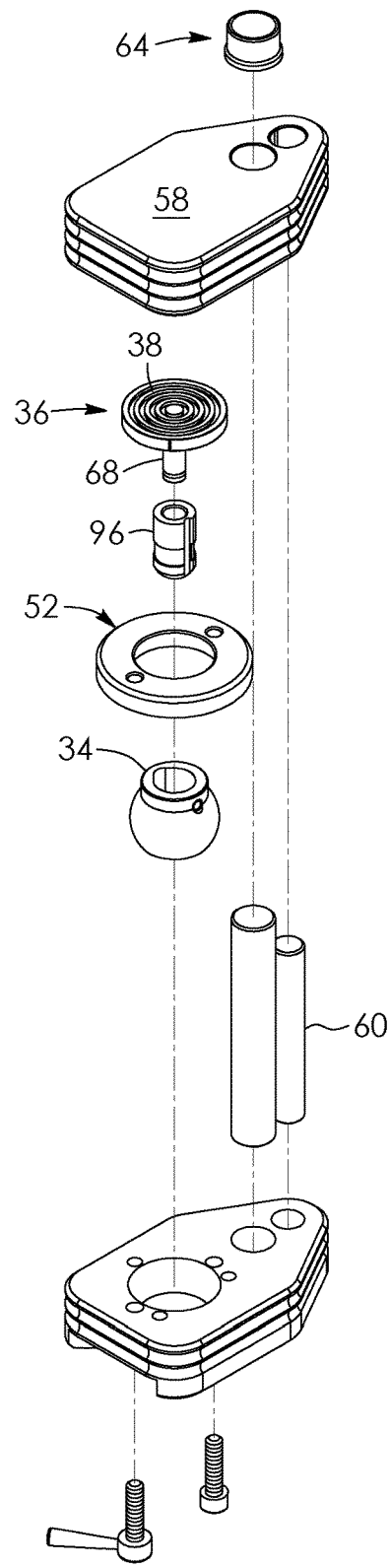
FIG. 4B is an exploded view of the tool shown in FIG. 3A.

Referring to FIG. 4B, there is shown a bi-axial pivoting assembly 32. The bi-axial pivoting assembly 32 is operatively connected to one of the chuck receiver 34 or the positioning assembly 40. The bi-axial pivoting assembly 32 may include a rotatable joint or any other joint assemblies, such as a ball-joint assembly. It may also include controllable servo-motors or any other controllable devices capable of orienting the positioning assembly 40 in a complementary position according to a given angle. Optionally, a locking mechanism 44 can be used to lock the bi-axial pivoting assembly 32 in a complementing position. A high friction connection between the bi-axial pivoting assembly and the base could also serve as a locking mechanism.

Figure 2B:
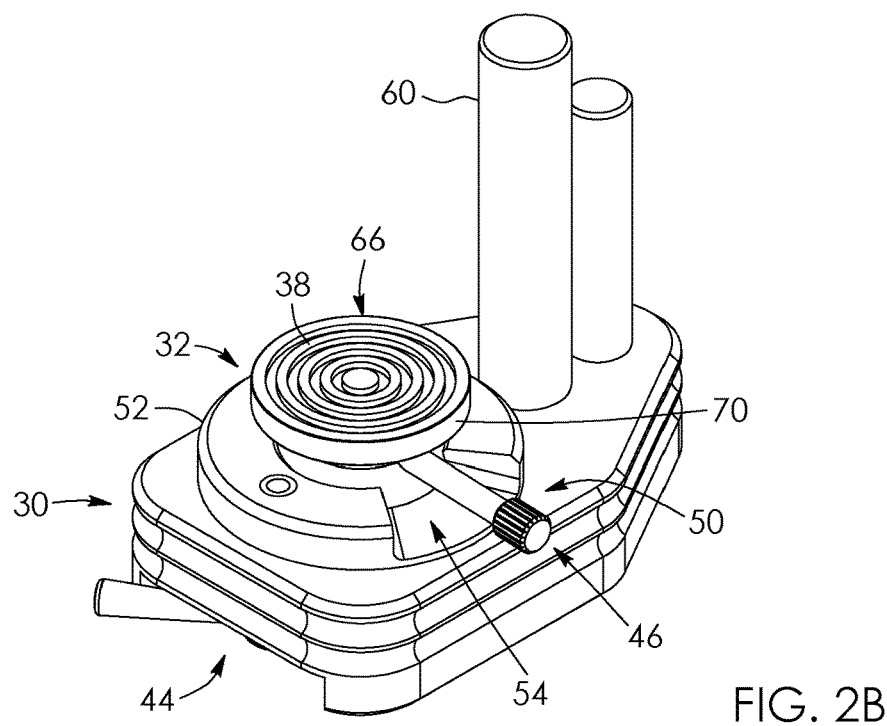
FIG. 2B is another perspective view of FIG. 2A, with an element of the tool removed.
Figure 2C:
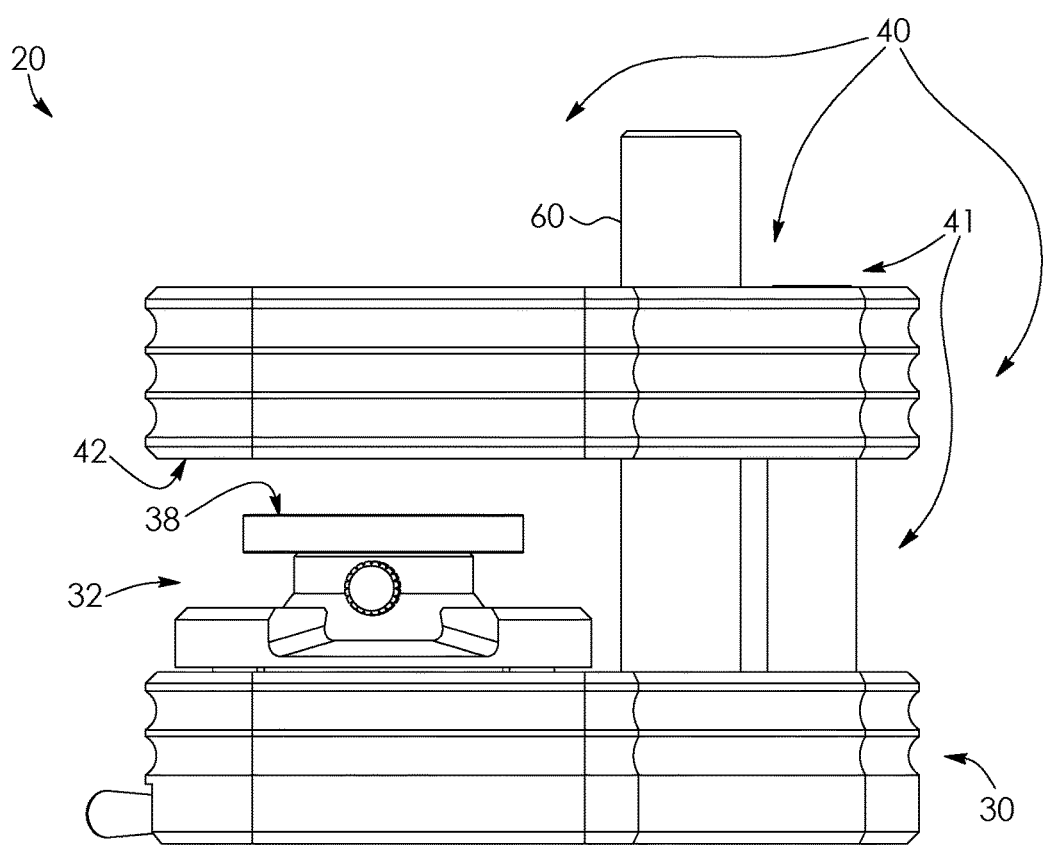
FIG. 2C is a side view of the tool of FIG. 2A.

In the first scenario, where the bi-axial pivoting assembly can be mounted between the base 30 and the chuck receiver 34 as illustrated in FIGS. 2B and 5D. In use, the chuck can be oriented such that the upper face of the tissue block/embedding block (24, 74) is coplanar with the flat surface 42 of the positioning assembly 40 and therefore capturing an angle between the upper surface (24, 74) and the flat surface 42 or tilting the bi-axial pivoting assembly 40 according to a compensating angle indicative of the correction to make.

In the second scenario, the bi-axial pivoting assembly can be operatively mounted on the positioning assembly 40. In this case, the chuck receiver can be mounted on the base 30 such as the orientation of the chuck when placed in the chuck receiver is fixed and can be used as a reference plane. In use, the bi-axial pivoting assembly be oriented such as the flat surface 42 of the positioning assembly 40 is coplanar with the upper face of the tissue block/embedding block (24, 74) in order to capture the angle between the upper surface (24, 74) and the flat surface 42 or tilting the bi-axial pivoting assembly 40 according to a compensating angle indicative of the correction to make.

The tool 20 may also include the chuck 36 wherein said chuck 36 has a platform 66 and a stem 68 extending therefrom, and wherein the platform 66 has a sidewall 70 that is provided with a groove 72. The groove 72 can be used for positioning the chuck 36 in a predetermined orientation. Using the groove 72 as a marker, the chuck 36 can be placed in the chuck receiver 34 with the same orientation in the steps of determining the misalignment angle formed by the cutting plane 26 and of remodeling the tissue block 22 for compensating the misalignment angle, as described below.

Numerous other modifications could be made to the above-described alignment method without departing from the scope of the present invention. The above-described embodiments are considered in all respect only as illustrative and not restrictive, and the present application is intended to cover any adaptations or variations thereof, as apparent to a person skilled in the art.

The above-described embodiments are considered in all respect only as illustrative and not restrictive, and the present application is intended to cover any adaptations or variations thereof, as apparent to a person skilled in the art. Of course, numerous other modifications could be made to the above-described embodiments without departing from the scope of the invention, as apparent to a person skilled in the art.

The invention claimed is:

1. A tool for applying a correction on a resection margin of a tissue block having a top surface, in order to align the resection margin with the cutting plane of a microtome, the correction being determined using an embedding block having been cut by the microtome so as to define a cut face, the tool comprising:
a base;
a chuck receiver operatively mounted to the base for receiving a chuck having a top surface for supporting the embedding block or the tissue block;
a positioning assembly comprising a movable plate having a flat surface, the movable plate being configured so that its flat surface can be pressed on the cut face of the embedding block or on the outer surface of the tissue block when the chuck supporting the embedding block or the tissue block in mounted to the base;
a bi-axial pivoting assembly operatively connected to one of the chuck receiver and the positioning assembly, the movable plate of the positioning assembly and the chuck receiver being movable one relative to the other for pressing the embedding block between the flat surface of the movable plate and the top surface of the chuck, for tilting the bi-axial pivoting assembly according to a compensating angle indicative of the correction to make; and
a locking mechanism to lock the bi-axial pivoting assembly in a complementing position in which the flat surface of the movable plate is pressed on the cut face of the embedding block when the chuck supporting the embedding block is mounted to the base, and when the chuck supporting the tissue block is mounted to the base, the locking mechanism is locked in the complementing position, the flat surface of the movable plate thereby remodelling the top surface of the tissue block with the compensating angle.

2. The tool according to claim 1, wherein the bi-axial pivoting assembly is mounted to the base and comprises the chuck receiver.

3. The tool according to claim 1, wherein the positioning assembly is lowerable toward the bi-axial pivoting assembly, for pressing the embedding block between the flat surface of the positioning assembly and the top surface of the chuck, when the chuck supporting the embedding block is mounted to the base.

4. The tool according to 1, wherein the bi-axial pivoting assembly comprises a ball-joint assembly.

5. The tool according to claim 1, wherein the tool further comprises a chuck locking mechanism mounted on the chuck receiver, configured to lock the chuck in the chuck receiver.

6. The tool according to claim 1, wherein the chuck receiver 34 comprises a threaded aperture and a locking pin, the threaded aperture receiving the locking pin to lock the chuck in the chuck receiver.

7. The tool according to claim 1, wherein the movable plate comprising a top surface and the flat surface, wherein the movable plate has a tapered end providing increased clearance when removing the chuck from the chuck receiver.

8. The tool according to claim 1, wherein the positioning assembly comprises a guiding assembly mounted onto to the base, configured to cause the positioning assembly to move perpendicularly to the base.

9. The tool according to claim 8, wherein the guiding assembly comprises at least one shaft mounted perpendicular onto to the base and the plate comprising a corresponding aperture for receiving each of the least one shaft, the at least one shaft allowing the positioning assembly to slide thereon.

10. The tool according to claim 9, wherein the least one shaft and the plate are removably connected.

11. The tool according to claim 9, wherein the plate has the top surface opposite to the flat surface, the plate comprising at least one flange positioned coaxially with each aperture extending outwardly from each surface of the positioning assembly in order to maintain the flat surface perpendicular to the at least one shaft.

12. The tool according to claim 1, further comprising the chuck, the chuck comprising a platform and a stem extending therefrom and wherein the platform has a sidewall provided with a groove for positioning the chuck in a predetermined orientation.

13. A method for aligning a resection margin of a tissue block with the cutting plane of a microtome in a cryostat, comprising the steps of:
a) providing an embedding block having opposed first face and second face, the second face resting on the top surface of a chuck;
b) placing the chuck in the microtome and cutting the first face of the embedding block, the cut first face of the embedding block forming thereafter an angle with the top surface of the chuck, the angle corresponding to a compensating angle between the top surface of the chuck and the cutting plane of the microtome;
c) determining an angle formed between the cut first face of the embedding block and the top surface of the chuck thereby corresponding to a misalignment angle; and
d) placing the chuck in a tool comprising a positioning assembly, the positioning assembly comprising a flat surface, the tool positioning the top surface of the chuck at an angle corresponding to the misalignment angle relative to the flat surface of the positioning assembly.

14. The method according to claim 13, wherein step c) comprises the sub-steps of:
i) placing the chuck with embedding block cut in step b) in a tool comprising a bi-axial pivoting assembly;
ii) lowering a horizontal flat surface toward the bi-axial pivoting assembly until the horizontal flat surface presses on the cut first face of the embedding block, thereby tilting the bi-axial pivoting assembly in a complementing position, an angle formed between the horizontal flat surface of the positioning assembly and the top surface of the chuck thereby corresponding to a misalignment angle; and
iii) locking the bi-axial pivoting assembly in the complementing position and removing the embedding block from the tool.

15. The method according to claim 13, wherein in step b), cutting the first face of the embedding block is made by cutting an entire surface of the first face.

16. The method according to claim 13, wherein in step a), the embedding block solely comprises embedding medium.

17. The method according to claim 13, further comprising the steps of:
e) placing a tissue sample previously frozen and flattened on the top surface of the chuck;
f) embedding the tissue sample with embedding medium to form the tissue block having opposed first face and second face, the first face of the tissue block corresponding to the resection margin of the tissue sample, the second face resting on the top surface of the chuck,
g) placing the chuck with the tissue block in the tool comprising the positioning assembly;
h) moving the horizontal flat surface relative to the first face of the tissue block until the horizontal flat surface presses on the first face of the tissue block, thereby remodeling the tissue block such that the first face of the tissue block being parallel to the flat surface and forming a remodeling angle between the first face of the tissue block and the top surface of the chuck, said angle corresponding to the misalignment angle;
i) allowing the embedding medium of the tissue block to freeze; and
j) removing the chuck from the tool and placing the chuck in the microtome for cutting layers of the tissue block, the first face of the tissue block remodeled in step h) being therefore parallel to the cutting plane of the microtome, the misalignment angle of the tissue block cancelling the compensating angle between the cutting plane and top surface of the chuck.

18. The method according to claim 13, wherein in step a), the embedding block corresponds to the tissue block.

* * * * *